United States Patent
Gupta et al.

(10) Patent No.: US 11,812,922 B2
(45) Date of Patent: *Nov. 14, 2023

(54) METHODS AND APPARATUS FOR SURGICAL FASTENING

(71) Applicant: C.R. Bard, Inc., Murray Hill, NJ (US)

(72) Inventors: Saurav V. Gupta, Medway, MA (US);
Kevin J. Ranucci, Warwick, RI (US);
Derek J. Leatzow, Chicago, IL (US);
Keith A. Grider, Chicago, IL (US)

(73) Assignee: C.R. Bard, Inc., Murray Hill, NJ (US)

( * ) Notice: Subject to any disclaimer, the term of this patent is extended or adjusted under 35 U.S.C. 154(b) by 313 days.

This patent is subject to a terminal disclaimer.

(21) Appl. No.: 17/110,881

(22) Filed: Dec. 3, 2020

(65) Prior Publication Data
US 2021/0085324 A1  Mar. 25, 2021

Related U.S. Application Data

(60) Continuation of application No. 16/375,145, filed on Apr. 4, 2019, now Pat. No. 10,856,872, which is a division of application No. 14/075,524, filed on Nov. 8, 2013, now Pat. No. 10,285,697.

(51) Int. Cl.
*A61B 17/10* (2006.01)
*A61B 17/068* (2006.01)
*A61B 17/064* (2006.01)

(52) U.S. Cl.
CPC ............ *A61B 17/10* (2013.01); *A61B 17/068* (2013.01); *A61B 2017/0649* (2013.01)

(58) Field of Classification Search
CPC .......... A61B 17/068; A61B 2017/0649; A61B 17/10; A61B 17/064; A61B 2017/0647; A61B 2017/0648
See application file for complete search history.

(56) References Cited

U.S. PATENT DOCUMENTS

| | | | |
|---|---|---|---|
| 4,762,453 A | 8/1988 | DeCaro |
| 4,917,554 A | 4/1990 | Bronn |
| 5,904,696 A | 5/1999 | Rosenman |
| 7,189,251 B2 | 3/2007 | Kay |
| 7,862,573 B2 | 1/2011 | Darois et al. |

(Continued)

FOREIGN PATENT DOCUMENTS

| | | |
|---|---|---|
| EP | 1 990 014 A2 | 11/2008 |
| GB | 2 417 208 A | 2/2006 |

(Continued)

OTHER PUBLICATIONS

EP14192141.1, Mar. 13, 2015, Extended European Search Report.
Extended European Search Report for European Application No. 14192141.1, dated Mar. 13, 2015.

*Primary Examiner* — George J Ulsh
(74) *Attorney, Agent, or Firm* — Wolf, Greenfield & Sacks, P.C.

(57) ABSTRACT

A surgical fastener deployment system may include a plurality of coil fasteners having a head and coil body. In one embodiment, the head may be larger in diameter than the coil body. The fasteners may also be mounted on a guide rod or mandrel that passes through a through-hole of the head and the coil body. The shaft may also include a guiding element that contacts and stabilizes the coil body as the fastener is deployed from a distal end of the shaft. When the head approaches and contacts the guiding element, the guiding element may deflect to permit the head to pass.

23 Claims, 5 Drawing Sheets

(56) References Cited

U.S. PATENT DOCUMENTS

| | | |
|---|---|---|
| 7,867,252 B2 | 1/2011 | Criscuolo et al. |
| 8,087,142 B2 | 1/2012 | Levin et al. |
| 8,343,176 B2 | 1/2013 | Criscuolo et al. |
| 8,382,778 B2 | 2/2013 | Criscuolo et al. |
| 10,285,697 B2 | 5/2019 | Gupta et al. |
| 10,856,872 B2 | 12/2020 | Gupta et al. |
| 2007/0038220 A1 | 2/2007 | Shipp |
| 2008/0281353 A1 | 11/2008 | Aranyi |
| 2009/0204129 A1 | 8/2009 | Fronio |
| 2010/0274266 A1 | 10/2010 | Rimer et al. |
| 2011/0087240 A1 | 4/2011 | Shipp |
| 2011/0092992 A1 | 4/2011 | Darois et al. |
| 2011/0295282 A1 | 12/2011 | Glick et al. |
| 2012/0022557 A1 | 1/2012 | Cabiri et al. |
| 2012/0160896 A1 | 6/2012 | Houard |
| 2013/0131700 A1 | 5/2013 | Criscuolo et al. |
| 2014/0243855 A1 | 8/2014 | Sholev et al. |
| 2015/0133965 A1 | 5/2015 | Gupta et al. |
| 2019/0223870 A1 | 7/2019 | Gupta et al. |

FOREIGN PATENT DOCUMENTS

| | | |
|---|---|---|
| WO | WO 2004/112841 A2 | 12/2004 |
| WO | WO 2007/098512 A1 | 9/2007 |
| WO | WO 2008/010948 A2 | 1/2008 |
| WO | WO 2013/046115 A1 | 4/2013 |

Sec. B-B

METHODS AND APPARATUS FOR SURGICAL FASTENING

RELATED APPLICATIONS

This Application is a Continuation of U.S. application Ser. No. 16/375,145, filed Apr. 4, 2019, which is a Divisional of U.S. application Ser. No. 14/075,524, filed Nov. 8, 2013, the disclosures of each of which are incorporated herein by reference in their entirety.

FIELD

Aspects relate to methods and apparatus for surgical fastening.

BACKGROUND

Surgical fasteners are widely used in many different medical procedures. For example, staples, sutures, clips and other fasteners are commonly used in laparoscopic and open surgical procedures.

SUMMARY

According to one embodiment, a surgical fastener deployment system includes a first shaft including a proximal end and a distal end. The first shaft is configured to contain at least one coil fastener including a head attached to a coil body extending from the head. The surgical fastener deployment system also includes a guiding element constructed and arranged to guide the coil body of the at least one coil fastener and to deflect out of the path of the head of the at least one coil fastener as the at least one coil fastener is are moved in a distal direction.

According to another embodiment, a method for deploying a surgical fastener includes: rotating and distally displacing a coil fastener within a first shaft in order to deploy the coil fastener, wherein the coil fastener comprises a head attached to a coil body extending from the head; contacting the coil body of the coil fastener with a guiding element during deployment of the surgical fastener; and deflecting the guiding element out of the path of the head of the coil fastener during deployment of the coil fastener.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. Various embodiments of the invention will now be described, by way of example, with reference to the accompanying drawings, in which.

DETAILED DESCRIPTION

The inventors have appreciated that conventional coil fasteners may be overdriven during deployment. In applications such as attachment of a prosthetic to tissue, overdriving a typical coil fastener may result in the coil fastener passing completely through the prosthetic and into the underlying tissue. As a result, the fastener is simply deployed into tissue without attaching the prosthetic to the tissue. In view of the above, the inventors have appreciated that providing a coil fastener with an associated head having a transverse dimension, such as a diameter, larger than that of the coil body may help to increase visibility of the fastener and help to reduce the occurrence of overdriving of the fastener.

Typically, coil fasteners without an associated head have uniform diameters along their lengths and are guided during deployment by an associated threaded shaft or mandrel that engages with each of the coil windings of the coil fastener. In addition to guiding the coil fasteners during deployment, engaging the coil windings of the fastener may help to stabilize the coil fastener as it is deployed into a prosthetic and/or tissue. For example, stabilizing the coil fastener may help to prevent undesired compression of the fastener and ensure proper insertion into a target prosthetic and/or tissue by preventing axial deflection and/or radial expansion of the coil fastener. However, in some embodiments, only the head of the fastener is guided and stabilized. Consequently, the coil windings of the surgical fastener may not be directly supported by the associated shaft or mandrel. Therefore, during deployment, as the distal end of the coil fastener is deployed into a target prosthetic and/or tissue, the coil body is left unsupported and free to compress, deflect laterally, and/or expand radially. As a result, the distal end of the coil fastener may deflect laterally (e.g. to the side) and may enter the prosthetic and/or tissue at an angle and/or undesired position. The coil may also expand radially (e.g. the coil will expand to a larger diameter) and may enter the prosthetic and/or tissue in an unintended radial location. Alternatively, or in addition, the coil may compress against and/or skive across the tissue rather than penetrating into it, particularly when the coil encounters harder tissue such as bone.

In view of the above, the inventors have recognized the benefits associated with devices and methods capable of stabilizing a headed coil fastener as the fastener is deployed into a prosthetic and/or tissue. For example, in one specific embodiment, a guiding element such as a deflectable latch may be used to guide the coil body as the distal end of the fastener is deployed into tissue. Once the head of the fastener reaches the latch, the latch may deflect laterally to permit the head to pass.

For the sake of clarity, the embodiments depicted in the figures are directed to a laparoscopic device. However, the current disclosure is not limited to laparoscopic devices. Instead, the currently disclosed devices and methods could be used in any appropriate device for the deployment of a surgical fastener into tissue. For example, the surgical fasteners could be used in an endoscopic device, a borescopic device, a catheter, a deployment device for use in "open" procedures, or any other appropriate deployment device. Additionally, the surgical fasteners might be used individually, or a plurality of surgical fasteners could be used.

For the purposes of this application, a transverse dimension of the coil body or head generally refers to a dimension of the coil body or head within a plane that is perpendicular to a long axis of the surgical fastener when it is assembled (e.g. a diameter of a cylindrical coil body, a width of a rectangular head, the length of a side of a triangular coil body, etc. . . . ). For example, an outer transverse dimension of the coil body would refer to the lateral distance between opposing outer surfaces of the coil body and an inner transverse dimension of the coil body would refer to the lateral distance between opposing interior surfaces of the coil body. The outer transverse dimensions of the head $T_H$ and coil body $T_C$ in one embodiment are illustrated in FIG. 2B and correspond to the width of the head and the diameter of the coil body. It should be noted that in embodiments in which the head and/or the coil body are noncircular, the head and/or coil body may have both minimum and maximum transverse dimensions.

Figure 1:
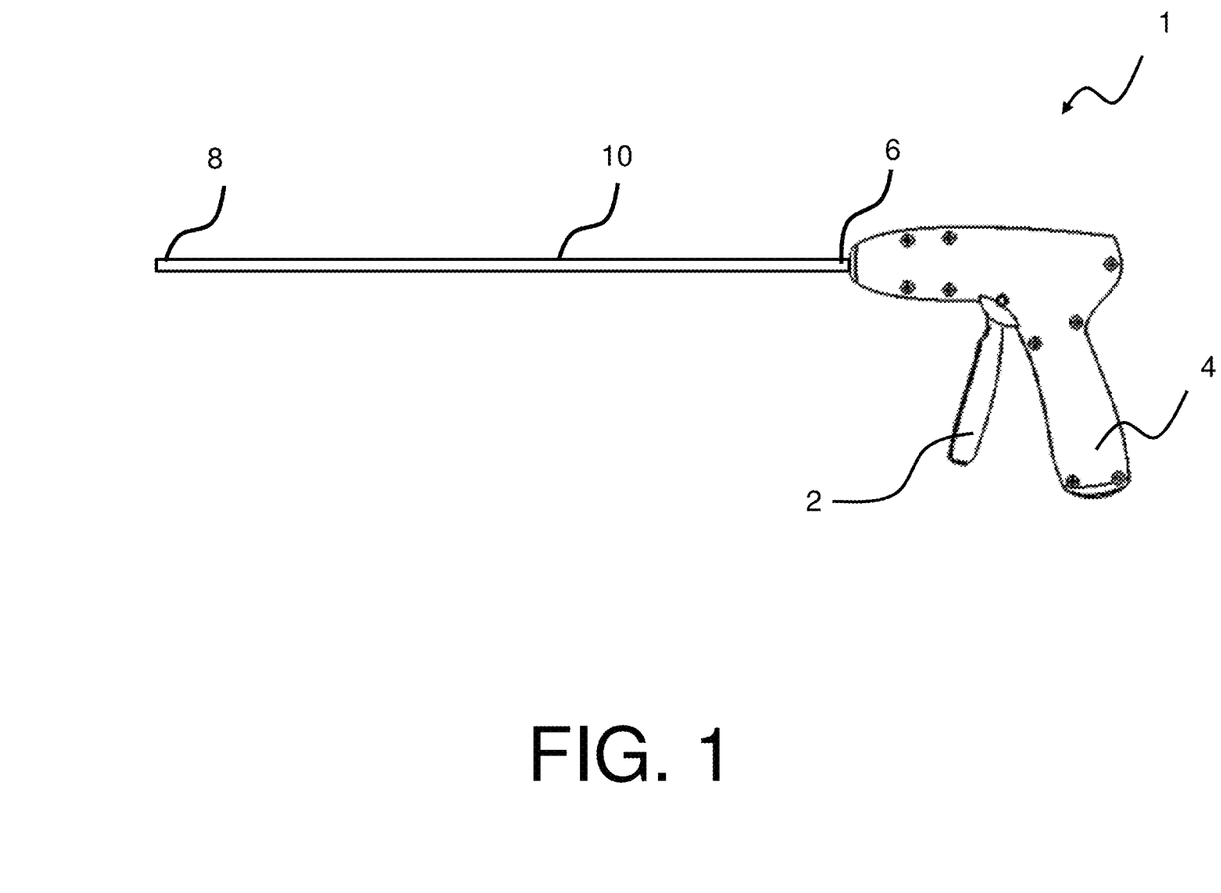
FIG. 1 depicts a fastener deployment device that may be used to deploy surgical fasteners in accordance with an aspect of the invention.

FIG. 1 depicts an exemplary fastener deployment device 1 for deploying one or more surgical fasteners into a prosthetic and/or tissue. The deployment device includes a handle 4 at a proximal end of the device and an actuation button such as a trigger 2 on the handle. The deployment device also includes a shaft 10 extending in a distal direction from the handle 4. The shaft 10 has a proximal end 6 and a distal end 8. Actuating the trigger 2 deploys a distal-most surgical fastener from the distal end 8 of the shaft 10. Actuation of the trigger 2 may also advance one or more surgical fasteners towards the distal end of the shaft 10. It should be understood that the deployed surgical fastener may be deployed into any appropriate prosthetic, bone, and/or tissue. For example, in one embodiment, the prosthetic may be a soft tissue repair fabric, such as a surgical mesh, used for repairing a hernia.

Figure 2A:
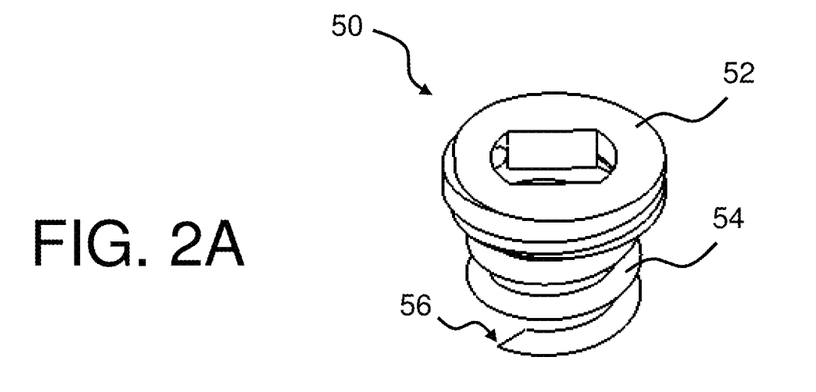
FIG. 2A depicts a coil fastener with an enlarged head in accordance with an aspect of the invention.
Figure 2B:
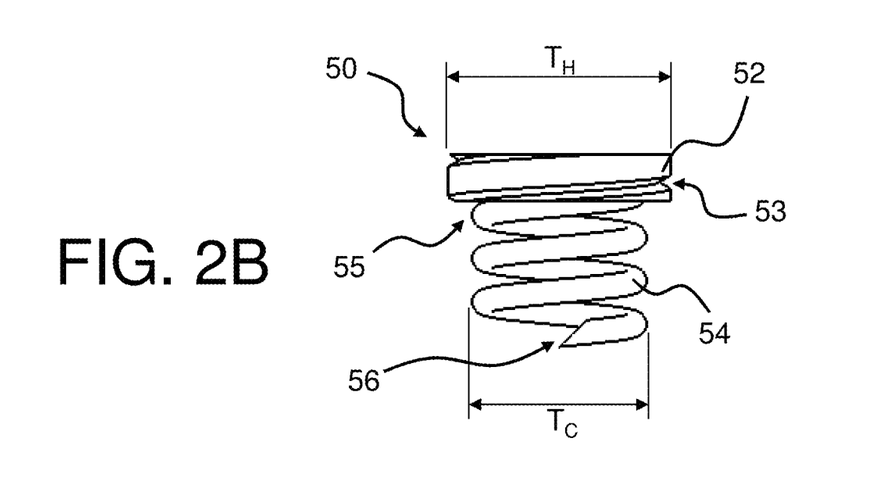
FIG. 2B depicts a side view of the coil fastener of FIG. 2A.
Figure 2C:
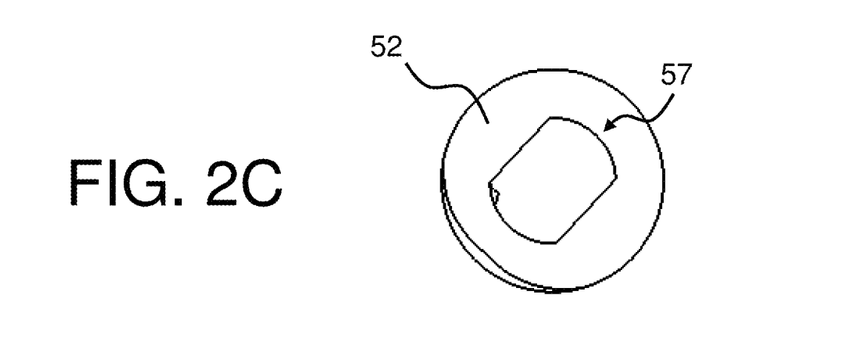
FIG. 2C depicts a top view of the coil fastener of FIG. 2A.

FIGS. 2A-2C depict one embodiment of a coil fastener 50 including a head 52 attached to a distally extending coil body 54. More specifically, the coil body 54 has a proximal end 55 attached to the head 52 and a distal tip 56 adapted for insertion into a prosthetic and/or tissue. As depicted in the figure, the distal tip 56 may be sharp to facilitate penetration into an appropriate prosthetic, bone, and/or tissue. As shown in FIG. 2C, the head 52 may also include a through-hole 57 for accepting an associated guide rod or mandrel, as discussed in more detail below. The coil body 54 may be attached to the head 52 using any appropriate method. For example, the coil body 54 may be integral with the head 52 or it may be manufactured separately and attached using a compression fit, adhesives, mechanical interlocking features, threading, interference fits, or any other appropriate method.

In the depicted embodiment, and as best seen in FIG. 2B, the head 52 includes externally located threads 53 that engage with an associated threaded shaft as described below. The depicted head 52 has a maximum transverse dimension $T_H$ (e.g. a diameter) that is greater than a maximum transverse dimension $T_C$ of the coil body 54. The threads 53 on the head 52 may have a helix angle and/or pitch that is the same as the helix angle and/or pitch of the coil body 54. Alternatively, the threads 53 on the head 52 may have a helix angle and/or pitch that is different than the coil body 54 as the current disclosure is not limited in this fashion. While the depicted coil fastener includes a head with an external thread for engaging a threaded shaft or other appropriate component, in an alternative embodiment, the head may include an internal thread in the through-hole 57 for engaging a threaded mandrel or other appropriate component.

Figure 3A:
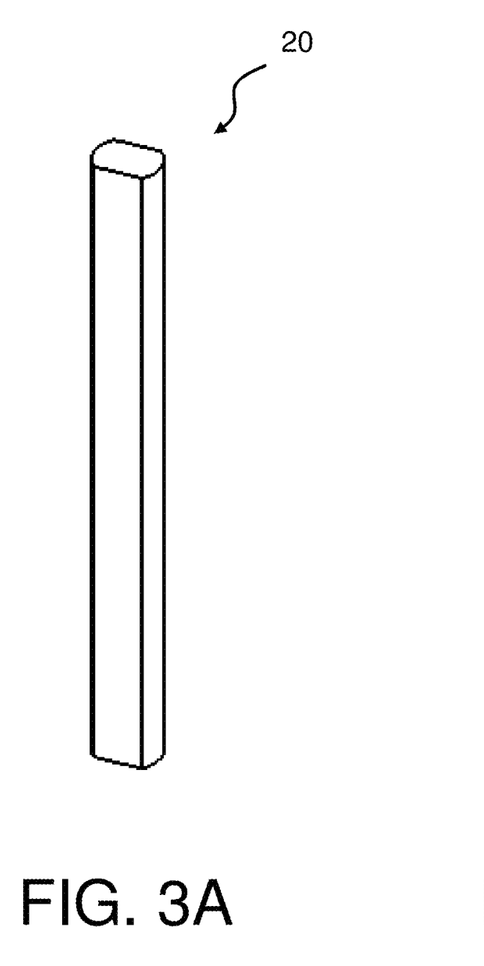
FIG. 3A depicts a guide rod that may be used in the fastener deployment device of FIG. 1.
Figure 3B:
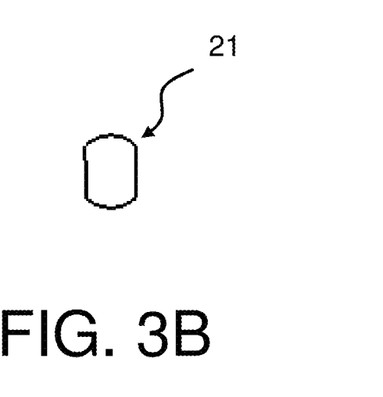
FIG. 3B depicts a cross-section of the guide rod of FIG. 3A.

One embodiment of a guide rod is shown in FIGS. 3A-3B. One or more coil fasteners may be mounted to a guide rod 20 by passing the guide rod through the center of the coil body 54 and the through-hole 57 of the coil fastener head 52. FIG. 3B shows the cross-section 21 of the guide rod 20, which may be uniform throughout the length of the guide rod though other embodiments in which the cross-section is not uniform along the length of the guide rod are also possible. As depicted in the figure, the guide rod 20 is shaped and sized to pass through the through-hole 57 of the coil fastener head 52 to permit distal movement of the coil fasteners along the length of the guide rod. In some embodiments, as shown in FIGS. 2C and 3B, a shape and size of the cross-section 21 of the guide rod 20 may complement a shape and size of the through-hole 57 of the fastener head 52. Further, in some embodiments, the guide rod 20 is rotatable on actuation of the deployment device. As the guide rod 20 is rotated, the cross-section 21 of the guide rod applies a torque to the through-hole 57 of the fastener head and rotates the fastener. Therefore, the guide rod 20 may act as a rotatable drive shaft in addition to supporting the coil fasteners. As depicted in the figures, the guide rod may include one or more flats to prevent rotation of the guide 20 relative to the fasteners mounted thereon and facilitate the application of the above noted torque. However, while a particular shape is depicted in the figures, other shapes including triangles, quadrilaterals, ovals, asymmetrical shapes, and other appropriate shapes are possible.

Figure 4A:
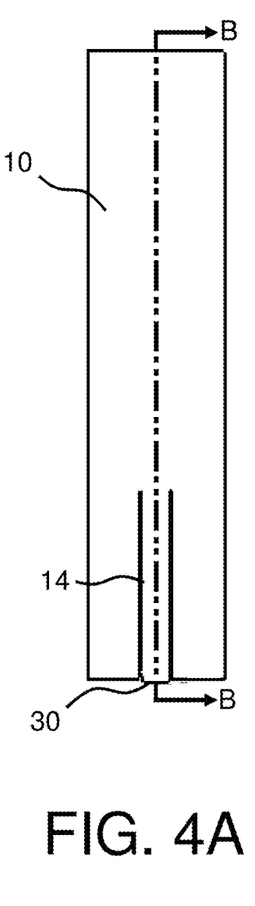
FIG. 4A depicts a side view of a shaft including a guiding element that may be used in the fastener deployment device of FIG. 1 in accordance with an aspect of the invention.
Figure 4B:
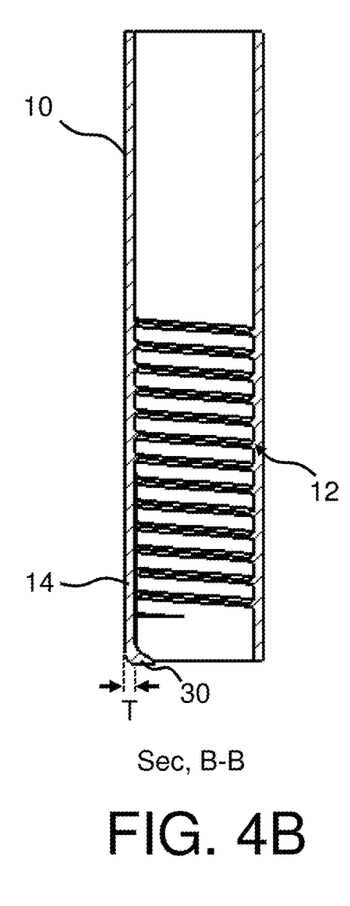
FIG. 4B depicts a cross-sectional view of the shaft of FIG. 4A taken along the line B-B.
Figure 4C:
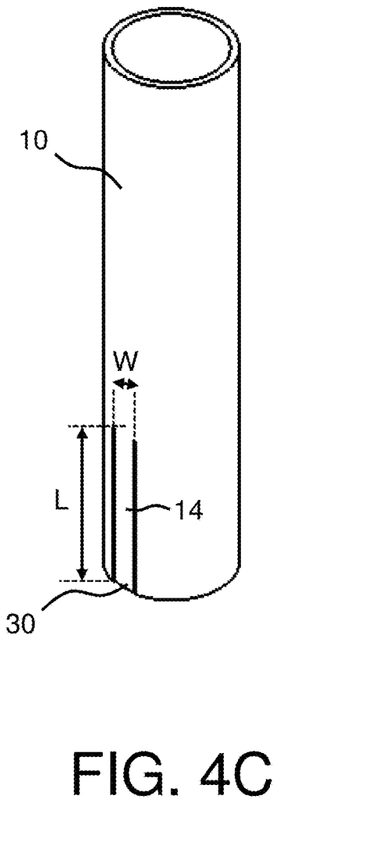
FIG. 4C depicts a perspective view of the shaft of FIG. 4A.
Figure 4D:
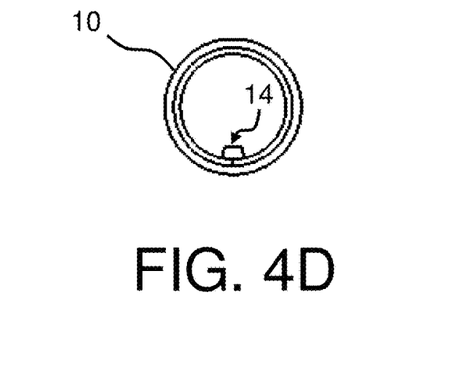
FIG. 4D depicts a top view of the shaft of FIG. 4A.

In some embodiments, the fastener deployment device includes a shaft. In the embodiment shown in FIGS. 3-5, the guide rod 20 is sized to pass through the shaft 10. As best seen in FIG. 4B, the inner surface of the shaft 10 includes threads 12 that are sized and arranged to correspond with the external threads 53 on the coil fastener head 52. As described in more detail below, the fastener deployment device also includes one or more guiding elements that stabilize the coil portions of the surgical fasteners as they are deployed and/or displaced through the deployment device. The guiding element may be constructed and arranged to prevent lateral expansion and/or deflection of the coil body of the fastener while still being capable of deflecting, or moving, out of the path of the associated fastener head.

In the embodiment shown in FIGS. 4A-4D, the shaft 10 includes a guiding element in the form of a deflectable latch 14 that stabilizes the coil body of the fastener as it is deployed out of the deployment device. Without wishing to be bound by any theory, a coil fastener experiences a normal reaction force from the tissue, bone, and/or prosthetic as the fastener abuts against and/or penetrates it. Such a reaction force may cause the coil body 54 to compress axially, expand laterally outwards, and/or deflect laterally outwards. As mentioned previously, in some cases, without a suitable guiding element, the coil body may simply compress against and/or skive across the prosthetic, bone, and/or tissue rather than penetrating it when the coil is deployed. Without wishing to be bound by theory, the coil body may tend to expand laterally when compressed. The presence of the guiding element 14 may prevent the coil body 54 from compressing, expanding, and/or deflecting laterally outwards, or limit any of the forgoing, which may thereby stabilize the position of the coil body as it is deployed into a tissue and/or prosthetic. As a result, the presence of the guiding element 14 may constrain the coil body such that it moves distally and penetrates through prosthetic, bone, and/or tissue rather than compressing against or skiving across it.

In some embodiments, the guiding element is constructed and arranged such that it may be deflected, or is otherwise displaced, out the path of the head of the coil fastener. For example, as described in more detail below, the latch 14 depicted in the figures is capable of deflecting radially outwards when the transversely larger fastener head contacts the latch 14. Therefore, the latch 14 may have sufficient stiffness to resist deflection in response to the load applied by the coil body and yet flexible enough to deflect when the fastener head contacts the latch. The stiffness of the latch 14 may be controlled using any appropriate design consideration including, but not limited to, material selection, geometry, and orientation.

In the embodiment shown in FIGS. 4A-4D, the latch 14 is a cantilever beam. As shown in the figures, the latch 14 may have a width W, a thickness T, and a length L. Without wishing to be bound by any theory, the deflection distance of a cantilever beam is inversely proportional to the area moment of inertia of the beam, which is a function of thickness T and width W, and is proportional to the length L of the beam. Therefore, larger thicknesses T and widths W will result in larger area moment of inertias and correspondingly smaller deflections of the latch 14 in response to a particular applied force. Additionally, larger lengths L of the latch 14 will give rise to larger deflections of the latch 14 in response to a particular applied force. Consequently, one of skill in the art, may select various combinations of length, width, and thickness of the latch to obtain a desired bending stiffness. For example, the width W, thickness T, and length L may be chosen such that the guiding element deflects a very small or insignificant amount when subjected to forces by the coil body and deflects a larger amount when subjected to the larger forces from the fastener head. By appropriately selecting the stiffness to provide the above noted behavior, the latch 14 may be capable of both supporting the coil body during deployment and deflecting out of the way to accommodate the fastener head.

Depending on the embodiment, the latch 14 may have any appropriate width W, thickness T, and length L based on particular design considerations as the current disclosure is not so limited. However, in one embodiment the width W of the latch 14 may be between about 0.3 mm to 3 mm. The latch 14 may also have a thickness T of 0.1 to 1 mm, 0.2 to 0.9 mm, 0.3 to 0.8 mm, 0.3 to 0.7 mm, 0.4 to 0.6 mm, or 0.45 mm to 0.55 mm, inclusive. Additionally, the latch 14 may have a length L between about 5.5 mm to 9 mm, 6 mm to 8.5 mm, 6.5 mm to 8 mm, or 7 mm to 7.5 mm, inclusive.

In the embodiment shown in FIG. 4B, the deflectable latch 14 includes a distal tip 30. The distal tip 30 of the latch 14 extends and/or points inwardly toward the exiting fasteners in order to contact the coil body 54 of the fastener. As will be discussed in detail below, the tip of the latch 14 stabilizes the coil fasteners by remaining tangent to the coil body of the fasteners as the fasteners are deployed. However, in some embodiments, the latch may have a protruding surface that points inwardly toward the fasteners at a location other than the distal end of the latch. As non-limiting examples, the latch may have a protruding surface in the middle of the latch, at a distance that is three-quarters the length of the latch, or at any suitable location. In some embodiments, the latch may have multiple protruding surfaces along the length of the latch in order to support multiple coil windings within the coil body 54.

The latch 14 may be provided in any appropriate manner. For example, the latch 14 may be integrally formed with a shaft such that the shaft and the latch comprise a single monolithic component. In such an embodiment, the latch might be formed by forming slits in a shaft to form a cantilever using any suitable process. In other embodiments, the latch may be manufactured separately and attached to the shaft by an adhesive, a welding process, or any other suitable method or substance, as this aspect is not so limited.

Other configurations of a guiding element are also contemplated. For example, the guiding element might be embodied by a flexible element located in the interior of the shaft and extending radially inwards from the shaft inner surface such that it engages with and supports the coil windings of the coil fastener. The flexible element may then deflect out of the path of the head of the coil fastener similar to the above embodiment. The flexible element may be embodied as a flexible rod attached to, and extending radially inwards from, the inner surface of the shaft. In another alternative embodiment, the guiding element may be embodied by a camming surface positioned in the shaft and constructed and arranged to interact with both the coil body and the head. The camming surface may also be associated with a radially directed compressible spring that is either positioned within, or passes through, the shaft and applies a biasing force to the camming surface to bias it inwards towards the center of the shaft. Therefore, as the fastener head is displaced and contacts the camming surface, the camming surface may be cammed radially outwards compressing the associated spring and accommodating the passage of the fastener head. In view of the above, it should be understood that the guiding element may be constructed in any appropriate fashion such that it both guides the coil windings of the coil fastener during deployment and accommodates the passage of a head associated with the coil fastener.

It should also be appreciated that the guiding element is not limited to being located on the shaft 10. In some embodiments, the fastener deployment device may have a second outer shaft that surrounds the aforementioned shaft 10. Consequently, a guiding element may be located on the second outer shaft and may stabilize the fastener as discussed previously. In other embodiments, a guiding element may be included at the distal end of the guide rod.

Figures 5A, 5B:
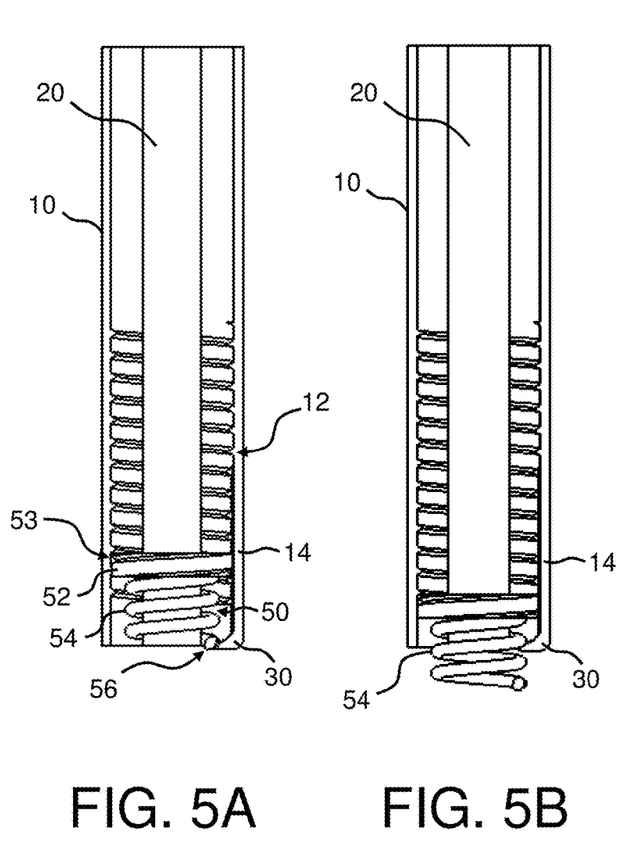
FIG. 5A depicts a fastener located at a distal opening of a shaft, the distal tip of the fastener contacting the distal tip of a deflectable latch.
FIG. 5B depicts the fastener of FIG. 5A exiting through the distal opening of the shaft.
Figure 5C:
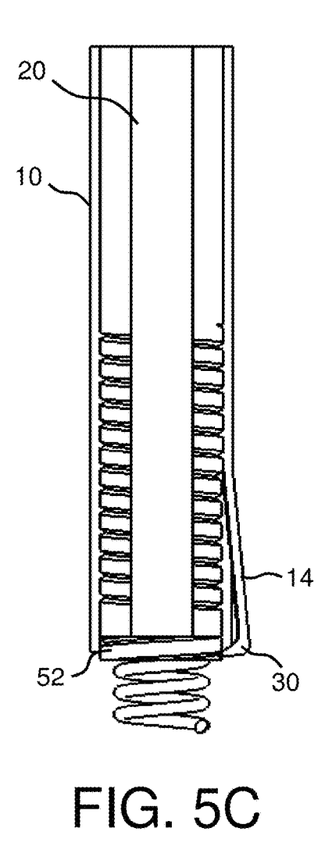
FIG. 5C depicts the latch of FIG. 5A deflecting out of the path of the head of the fastener as the head exits through the distal opening of the shaft.

The deployment of a fastener 50 using the shaft 10 and latch 14 of FIGS. 4A-4D is shown in three different stages in FIGS. 5A-5C. FIG. 5A depicts a guide rod 20 disposed within the shaft 10. The coil fastener 50 is mounted on the guide rod 20, which passes through the through-hole of the fastener head 52 and coil body 54. The external threads 53 of the head 52 are engaged with the threads 12 on the inner surface of shaft 10. The coil fastener 50 is also located at the distal end of both the shaft 10 and guide rod 20 such that the distal tip 56 of the fastener 50 is at an opening of the shaft 10 and is in contact with the distal tip 30 of the latch 14. The distal tip 30 of the latch 14 may extend and/or point inwardly toward the exiting fasteners in order to contact the coil body 54 of the fastener. While a single coil fastener 50 has been depicted for the sake of clarity, any number of coil fasteners could be held within shaft 10. Further, as noted above, while a latch 14 has been depicted for the guiding element, any suitable guiding element may be used.

As shown in FIG. 5B, when the fastener 50 is rotated and moved in the distal direction relative to the shaft 10 and associated latch 14, the tip 30 of latch 14 remains tangent to and guides the coil body 54 as it rotates against and slides past the latch tip 30. In the embodiment shown in the figures, the latch tip 30 is angled to correspond to the helix angle of the coil body 54. Such an angle on the latch tip 30 may help the latch tip 30 to remain tangent to the coil body 54 as the coil fastener is deployed. In other embodiments, the latch tip 30 may be flat or have an angle that differs from the helix angle of the coil body 54.

Finally, as shown in FIG. 5C, when the fastener head 52 approaches the latch tip 30, the head 52 applies a force to the tip 30 of the latch 14. In the depicted embodiment, the latch tip 30 acts as a camming surface such that contact between the fastener head 52 and the latch tip 30 during distal movement of the coil fastener causes the latch 14 to deflect outwards in a radial direction. Correspondingly, the force applied to the latch tip 30 during actuation deflects the latch 14 outwardly in a radial direction until it is out of the path of the head 52 and the fastener head 52 is able to be displaced in the distal direction.

As noted above, the functions of the guide rod and shaft may be reversed such that the shaft, or any other appropriate component, may be rotated to deploy the fasteners while the guide rod remains stationary. In such an arrangement, the guide rod may have a circular cross-sectional shape and may include threads. Correspondingly, the fastener head through-hole may be circular with internal threads that engage with the guide rod threads. Further, in such an embodiment, the fastener head may have a non-circular shape corresponding to a shape and size of the internal passage of the associated shaft. In such an embodiment, a guiding element may be located on the guide rod. However, the guiding element may also be located on the shaft and/or on another component such as a stationary second outer shaft that surrounds the aforementioned shaft.

While a single guiding element for guiding the coil fasteners has been depicted in the figures, a plurality of guiding elements for guiding the coil fasteners also is contemplated. For example, a plurality of latches or other guiding elements could be provided along a length of the deployment device to aid in guiding coil fasteners as they are distally moved through the shaft. Alternatively, or in addition to the above, a plurality of latches or other guiding elements could be associated with a coil fastener located in the distal most deployment position. In such an embodiment, the plurality of latches or other guiding elements at the end of the shaft may be radially spaced around the circumference of the shaft. The individual latches or other guiding elements may also be set at slightly different positions along the length of the shaft such that the latch tips engage with corresponding individual coil windings of the coil body of the distal most coil fastener. For example, a first latch could be located at the distal outlet of the shaft to guide the coil fastener as it is deployed into tissue and a second latch could be located half a coil fastener length up from the first latch to further stabilize the coil fastener during deployment. It should be understood that other arrangements are also possible.

The shaft may be made from aluminum, stainless steel, nickel alloys, titanium alloys, nickel titanium alloys, or any other suitable material, as this aspect is not so limited. The coil body of the fastener may be made from stainless steel, nickel titanium based alloys such as nitinol, titanium alloys, biocompatible and/or bioresorbable metals and bioresorbable polymers, or any other suitable material, as this aspect is not so limited. The guide rod may be made from stainless steel, a polymer, nickel alloys, titanium alloys, nickel titanium alloys, or any other suitable material. In some embodiments, if the latch or other guiding element is included on a shaft, the latch or other guiding element may be made of the same material as that of the shaft. However, in instances where the latch or other guiding element is made separately from the component it is assembled with, the latch or other guiding element may be made from aluminum, stainless steel, nickel titanium based alloys such as nitinol, titanium alloys, nickel alloys, polymers, or any other suitable material, as this aspect is not so limited.

The above aspects and embodiments may be employed in any suitable combination, as the present invention is not limited in this respect.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A surgical fastener deployment system comprising:
    a first shaft including a proximal end and a distal end, wherein the first shaft is configured to include at least one coil fastener disposed in the first shaft, wherein the at least one coil fastener includes a head attached to a coil body extending from the head, and wherein the at least one coil fastener includes a distal most coil fastener; and
    a guide including a deflectable latch at least partially oriented in a distal direction, and wherein a distal end of the deflectable latch includes at least one protruding surface that extends inwardly toward the coil body of the distal most coil fastener, and wherein the deflectable latch is located within one fastener length of a distal most end of the surgical fastener deployment system.

2. The surgical fastener deployment system of claim 1, further comprising the at least one coil fastener.

3. The surgical fastener deployment system of claim 2, wherein the coil body includes a plurality of coil windings, and wherein the coil windings include interior opposing surfaces disposed on opposite sides of a long axis of the coil fastener.

4. The surgical fastener deployment system of claim 1, wherein the deflectable latch comprises a cantilever.

5. The surgical fastener deployment system of claim 1, wherein the deflectable latch is integrally formed with the first shaft such that the first shaft and the deflectable latch comprise a single monolithic component.

6. The surgical fastener deployment system of claim 1, wherein the deflectable latch is formed by two slits in the first shaft along the distal length.

7. The surgical fastener deployment system of claim 1, wherein the deflectable latch is formed separately from the first shaft.

8. The surgical fastener deployment system of claim 1, wherein the guide is configured to prevent at least one selected from the group of compression, radial expansion, and lateral deflection of the coil body as the coil fastener is deployed from the distal most end of the surgical fastener deployment system.

9. The surgical fastener deployment system of claim 1, wherein the guide is located at the distal end of the first shaft.

10. The surgical fastener deployment system of claim 1, further comprising a guide rod positioned inside the first shaft, wherein the guide rod is shaped and configured to support the at least one coil fastener, and wherein rotation of the guide rod causes the at least one coil fastener to rotate and move towards a distal end of the first shaft.

11. The surgical fastener deployment system of claim 1, wherein the deflectable latch has a length of 5.5 mm to 9 mm.

12. The surgical fastener deployment system of claim 1, wherein the deflectable latch has a thickness of 0.1 mm to 1 mm.

13. The surgical fastener deployment system of claim 1, wherein the deflectable latch has a width of 0.3 mm to 3 mm.

14. The surgical fastener deployment system of claim 1, wherein the guide is configured to be in contact with the coil body as the at least one coil fastener is deployed into tissue.

15. A surgical fastener deployment system comprising:
- a first shaft including a proximal end and a distal end, wherein the first shaft is configured to include at least one coil fastener disposed in the first shaft, wherein the at least one coil fastener includes a head attached to a coil body extending from the head, and wherein the at least one coil fastener includes a distal most fastener;
- a plurality of guides, wherein the plurality of guides are spaced around at least a portion of a circumference of the first shaft, wherein the plurality of guides are spaced along at least a portion of a length of the first shaft, wherein each guide of the plurality of guides is located at a different longitudinal positional along the length of the first shaft, wherein the plurality of guides are configured to guide the coil body of the at least one coil fastener as the at least one coil fastener is moved in a distal direction out of a distal most end of the surgical fastener deployment system, and wherein the plurality of guides are configured to deflect out of a path of the head of the at least one coil fastener as the at least one coil fastener is moved in a distal direction; and
- a guide rod positioned inside the first shaft, wherein the guide rod is shaped and configured to support the at least one coil fastener, and wherein rotation of the guide rod causes the at least one coil fastener to rotate and move towards the distal most end of the first shaft.

16. The surgical fastener deployment system of claim 15, further comprising the at least one coil fastener.

17. The surgical fastener deployment system of claim 16, wherein the coil body includes a plurality of coil windings, and wherein the coil windings include interior opposing surfaces disposed on opposite sides of a long axis of the coil fastener.

18. The surgical fastener deployment system of claim 16, wherein the head has a maximum transverse dimension larger than a maximum transverse dimension of the coil body.

19. The surgical fastener deployment system of claim 15, wherein the plurality of guides comprises a first guide positioned at a distal most end of the first shaft.

20. The surgical fastener deployment system of claim 15, wherein the plurality of guides form a helical pattern along the portion of the first shaft.

21. The surgical fastener deployment system of claim 20, wherein a helix angle of the plurality of guides is equal to a helix angle of the coil body.

22. The surgical fastener deployment system of claim 15, wherein the plurality of guides comprises a first guide positioned at a distal most end of the first shaft and a second guide within one coil fastener length proximal of the first guide, wherein the first guide and the second guide are configured to engage the coil body of the distal most coil fastener as it is deployed out of the system.

23. The surgical fastener deployment system of claim 15, wherein the plurality of guides is configured to prevent at least one selected from the group of compression, radial expansion, and lateral deflection of the coil body as the coil fastener is deployed from the distal most end of the surgical fastener deployment system.

* * * * *